United States Patent
Mason et al.

(10) Patent No.: US 8,182,657 B2
(45) Date of Patent: May 22, 2012

(54) METHOD, INSTALLATION AND COMPONENT FOR DESTRUCTION OF LIVE ORGANISMS IN A LIQUID

(75) Inventors: Dennis Mason, Mjølkeråen (NO); Per-Ame Berger, Ulset (NO)

(73) Assignee: Environmental Solutions AS, Klerpesto (NO)

( * ) Notice: Subject to any disclaimer, the term of this patent is extended or adjusted under 35 U.S.C. 154(b) by 1435 days.

(21) Appl. No.: 10/578,170

(22) PCT Filed: Nov. 4, 2004

(86) PCT No.: PCT/NO2004/000333
§ 371 (c)(1),
(2), (4) Date: Oct. 4, 2006

(87) PCT Pub. No.: WO2005/042414
PCT Pub. Date: May 12, 2005

(65) Prior Publication Data
US 2007/0077166 A1 Apr. 5, 2007

(30) Foreign Application Priority Data
Nov. 4, 2003 (NO) .................................. 20034910

(51) Int. Cl.
*C02F 1/46* (2006.01)
(52) U.S. Cl. ...... 204/242; 204/267; 204/269; 204/275.1
(58) Field of Classification Search .................. 204/242, 204/267, 269, 275.1
See application file for complete search history.

(56) References Cited

U.S. PATENT DOCUMENTS

| | | | |
|---|---|---|---|
| 5,091,152 A | 2/1992 | Thomas | |
| 5,575,974 A | 11/1996 | Wurzburger et al. | |
| 5,851,375 A * | 12/1998 | Bodger et al. | 205/701 |
| 6,706,168 B2 * | 3/2004 | Igarashi | 205/744 |
| 2003/0136686 A1 | 7/2003 | Herbst | |

FOREIGN PATENT DOCUMENTS

| | | |
|---|---|---|
| DE | 41 00 799 A1 | 7/1992 |
| EP | 0765843 A1 | 4/1997 |
| EP | 0769475 A1 | 4/1997 |
| JP | 2002192161 | 7/2002 |
| SU | 842105 | 6/1981 |
| WO | WO 9604206 A1 | 2/1996 |
| WO | WO 03/059823 A1 | 7/2003 |

* cited by examiner

*Primary Examiner* — Arun S Phasge
(74) *Attorney, Agent, or Firm* — Francis C. Hand; Carella, Byrne, et al

(57) ABSTRACT

The invention relates to a method, a treatment installation (26) and a treatment component (29) for the destruction of microorganisms and macroorganisms in a flowing liquid. The destruction takes place instantaneously, while the liquid passes through said component (29) in said installation (26). The treatment is performed in that the liquid is led in a forced movement through a passage (49) in a case (48) of electrically insulating material. In flowing through the passage, the liquid is subjected to an influence from one or more alternating current fields in that alternating current is short-circuited in the flow of water through alternating current conductors (50) that are arranged internally in said case (48).

16 Claims, 11 Drawing Sheets

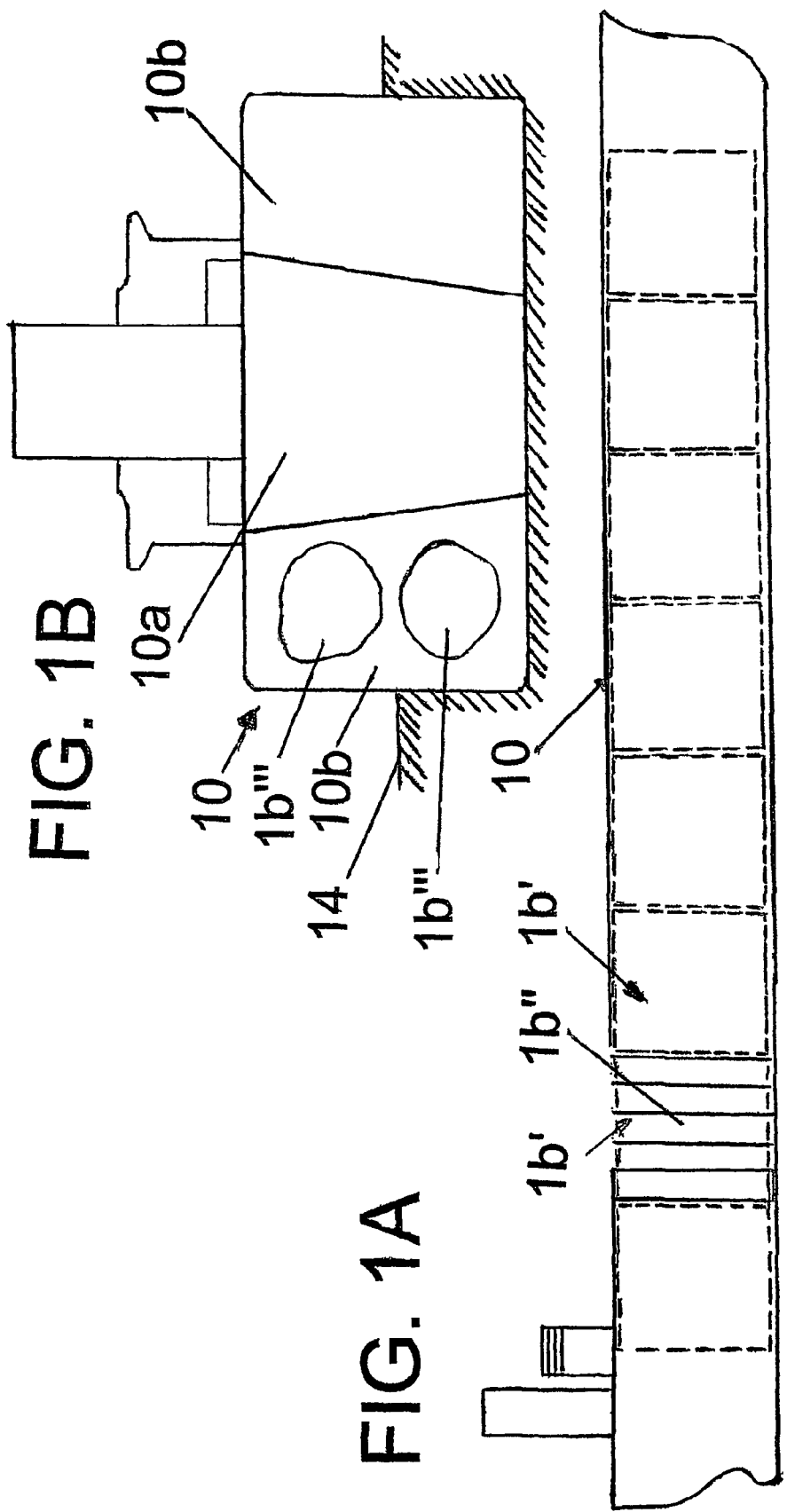

METHOD, INSTALLATION AND COMPONENT FOR DESTRUCTION OF LIVE ORGANISMS IN A LIQUID

The present invention relates to a method for treatment of a liquid that contains live organisms, where the treatment comprises destruction of live organisms as the liquid is in a treatment component in a treatment installation.

The invention also relates to a treatment installation and also a treatment component.

With the present invention one aims to generally destroy different species of live organisms that are present in a liquid.

Particularly implied with the expression live organisms are microorganisms and macroorganisms.

The expression microorganisms comprises single-cell organisms (protozoa), bacteria and so on, i.e. organisms that are so small that they cannot be seen without using a microscope, while other microorganisms, for example plankton, fungi and algae require a microscope for the determination of species.

Normally, one also considers and describes a virus as a microorganism, even if it is not clear whether it is correct to consider a virus as a live organism. It is known that a virus is dependent on its necessary association to other living organisms to be able to live and replicate itself. A virus is therefore normally found in a liquid as a "parasitic organism", i.e. in association with another live organism in the liquid or in the surroundings of the liquid, for example, in association with a microorganism or in association with a macroorganism.

With the expression macroorganisms various live organisms should be understood herein, which on the whole are visible to the naked eye, comprising organisms such as molluscs, shellfish, small fish and so on.

So far, according to prior art, one has essentially attempted to destroy live organisms that are present in a liquid by treatment of the liquid with chemicals or by initiating chemical processes in the liquid. Such known chemical treatment is relatively complicated and costly in operation and is rather time consuming. In addition, the effect of such chemical treatment has not given completely satisfactory results as for the extent of the destruction of live organisms.

Among other things it has been found that certain bacteria, such as Vibrio bacteria, have been especially difficult to destroy.

An addition of chemicals to the liquid often leads to the liquid being contaminated by such chemicals and that this again can have an adverse effect on the properties of the liquid and have an undesirable effect on the environment when the liquid is discharged at a designated location. In certain known treatment cases, the liquid gets an unacceptably high level of chlorine and other chemicals, making the liquid unsuited for ordinary use, for example, as for odour and of hazardous materials content.

It is also known to treat liquid, for example, ballast water and drainage water, by initiating electrochemical processes in the liquid to destroy live organisms present in the liquid. Solutions have been put forward by Marine Environmental Partners, Inc. (MEP), a company which is located in Florida, USA. What is special with electrochemical processes is that one can obtain a chemical reaction without having to necessarily use chemical additives, as the chemical processes can be developed by constituent parts or materials already present in the liquid.

Also, according to the present invention, one aims to treat a liquid without being dependent on addition of chemicals.

According to the invention one aims for a fast and especially effective destruction of the live organisms with simple means and with low operating costs.

The method according to the invention is characterised in that the liquid with the live organisms is subjected to an electron radiation as the liquid is led in a forced flow movement through an internal passage in the treatment component.

According to the invention an instantaneous destruction of microorganisms and macroorganisms is achieved in the liquid itself. By achieving instantaneous destruction of the liquid instead of subjecting the liquid to treatment over a period of hours or days, one achieves, according to the invention, considerable economic advantages. In addition, one obtains, according to the invention, a surprisingly good result from the treatment.

According to the invention, a special advantage is that one can quickly and simply treat even large amounts of liquid in an effective way. Further, the treatment according to the invention is advantageous in that it leads to a very satisfactory result based on relatively low consumation of electrical energy.

According to the invention, one can subject the liquid to a concentrated treatment in the local passage in the treatment component in the treatment installation with the result that all live organisms are instantaneously destroyed within a limited treatment area, i.e. in the said local passage in the treatment component, protected against unfortunate influences of the surroundings. With simple means one can consequently control the electron radiation within a limited area, without demonstrable electronic harmful effects in the surroundings of the treatment component.

In a practical solution according to the invention, the flow of liquid in the treatment component is guided through an electrically insulating case that surrounds the passage in the treatment component, as electron radiation is ensured by short circuiting at least one pair of conductors that are arranged on the inside of the electrically insulating case, in liquid contact with the conductors.

One aims to utilize the solutions according to the invention in many different application areas, i.e. industrial, health related and household related applications.

A relevant area of application, which shall be described in detail herein, is the treatment of ballast water.

In more detail, several of the areas of application, which are described in the following text, are based on treatment of different types of water. For example, the water can comprise of arbitrary types of seawater with various contents of microorganisms and macroorganisms. Alternatively, the water being treated according to the invention, can comprise of arbitrary types of fresh water or mixtures of seawater and fresh water. According to the invention, it can also be relevant to treat water with contents of other types of liquid. Further, one also aims to subject other liquids that contain microorganisms and/or macroorganisms to corresponding treatment for similar destruction of microorganisms and macroorganisms that are present in such liquids.

In a first case of application for treatment of ballast water the liquid is constituted by seawater that is collected from an arbitrary seawater source in a harbour area. Such harbour areas are especially used as a source for supply of ballast water to ships. It is common that ships are stabilised using ballast water so that the ship will take up the intended angle position at sea and the intended height position at sea. It is common, when the ship goes with ballast from the unloading site to a further unloading site or a new loading site, that the ballast tanks empty ballast water in the harbour area and fill ballast water in the ballast tank from the harbour area, respectively. It is known that ballast water in general constitutes a source of pollution of the surroundings in the harbour area where the ballast water is emptied out as the content of microorganisms and macroorganisms in the ballast water are spread out to surroundings which can be very sensitive to such dispersion, ecologically.

With regard to, for example, ballast water in ships of the size of 500,000 dwt., the ballast amount itself can constitute about ⅓, i.e. constitute an amount of water of about 150,000 to 160,000 tones. Such large amounts of water with a high content of live organisms can rapidly pollute the surroundings at the unloading site for ballast water.

At the terminal "Stureterminalen" in the county of Hordaland in Norway, 370 port of calls were registered in 1988. From these ships, 18,000,000 tonnes of ballast water were emptied into the harbour area, which were collected from a large number of various harbour areas in different parts of the world, each having their own ecological conditions and their own various species of microorganisms and macroorganisms. It is obvious that pollution of seawater in various harbour areas with ballast water represents considerable problems and that the present invention can make a considerable contribution to at least limit further pollution.

According to the embodiment example of treatment of ballast water, the present invention aims, amongst other things, to prevent or greatly reduce the danger of pollution of harbour areas where ballast water is being discharged. At the same time, it is also aimed to prevent spreading of unwanted content of live organisms in the ballast tanks themselves and in the pipe systems and so on onboard the ship.

According to the invention, the enforced control, for example, at treatment of ballast water, is based on handling of a liquid flow using pump power, as pump power is used, up until now, in regular installations for handling of ballast onboard a ship by regular filling of ballast water in ships and emptying of ballast water from ships, respectively.

It is common that the ballast handling installation onboard the ship comprises a permanent pipe connection between the sea side and the ballast tanks. It is also common that some kind of filtration system or a straining system for removal of different macroorganisms and so on, is connected to the pipe connection, but in practice it has been found that such filtration systems or straining systems are far from sufficient for this purpose.

In such known pipe connections, a powerful pump is also fitted, that pumps seawater, as ballast water, directly into the ballast tanks of the ship in a first harbour area and which, in a later sequence, pumps the ballast water out again into the sea in another harbour area, or, for example, partially directly out in the ocean during the travel from a first harbour area to a second harbour area.

According to the invention the treatment of ballast water onboard a ship can therefore easily be incorporated in a standard procedure for filling and emptying of ballast water, i.e. by utilisation of existing installations for handling ballast in an installation according to the invention. Destruction of live organisms can, according to the invention, be performed in a simple way by combining the liquid handling installation with a known, per se, ballast handling installation that is already in use onboard the ship.

The object according to the invention is, in the above mentioned embodiment example, according to the invention, in particular, to prevent that microorganisms and/or macroorganisms will spread in an uncontrolled way to the surroundings at the place of discharge during emptying of ballast water from the ship.

In another example of use, the water can be made up of drinking water, conducted in a pipeline network, for example, from a drinking water reservoir to the individual consumer. The enforced control which is used, according to the invention, for treatment of drinking water, can, for example, be based on a use of the water pressure in the pipeline network of the drinking water. Alternatively, the drinking water can, while flowing through the pipeline network, be subjected to a desired water pressure by using pump-stations that are arranged between the drinking water reservoir and the place of consumption. Treatment of drinking water in batches can also be performed in the course of flowing through the pipeline network to an arbitrary storage location or from the storage location to the consumer location itself, by using pump power or water pressure in the pipeline network for enforced control of the water in a treatment installation for such batch-wise treatment of the water. In a correspondingly advantageous way to that described for treatment of ballast water, an existing installation can, in an easy way, also be used in connection with treatment of drinking water, by a simple connection of the treatment component, according to the invention.

The object according to the invention concerning drinking water is especially to prevent that during tapping of drinking water, microorganisms and/or macroorganisms will disperse in an uncontrolled way through the pipeline network together with the drinking water to the consumer at the tapping location. An object in this context is to remove existing organisms in the drinking water itself and prevent or reduce collection of organisms in the pipeline network itself, respectively, thereby in different ways, prevent organisms that are present in the drinking water will be brought forward to the individual consumer.

In a third case of application, the water can be made up of drainage water or sewage from various types of activity areas. The sources for the drainage water or the sewage can, for example, constitute industrial companies, farms, small households such as hotels, bathing establishments, hospitals, special treatment plants or the like, respectively. In such cases, the enforced control can either be based on a flow of liquid which is subjected to a compressive force provided by the water pressure in the pipeline network of the drainage water and/or with the help of pump power connected to such a pipeline network.

In the third case, the object according to the invention is, in particular, to prevent that microorganisms and/or macroorganisms that are present in drainage water or sewage water, will disperse in an uncontrolled way to the surroundings via the pipeline network itself, or to streams, rivers, lakes or the sea and so on.

The method in a specially preferred embodiment example, according to the invention, is characterised in that the liquid during flowing through the pipe-formed passage is subjected to the influence of at least one alternating current field that is limited locally within the electrically insulating case which surrounds the pipe-formed passage, and that the mentioned alternating current field is imposed between conductors that are arranged across the flow of liquid to activate the flow of liquid in the cross section of the flow in the passage.

In a surprising way, according to the invention, it has been found possible to destroy all organisms that are present in the liquid flow in an easy way by using alternating current fields in the treatment component. According to the invention, the flow of liquid is influenced by the said alternating current field in a local area being limited inside the axial extension of the pipe-formed passage in the treatment component, in that the passage in the mentioned area is surrounded by the mentioned electrically insulating case.

According to the invention, by establishing electron radiation in the form of continuous short-circuiting of alternating current through an alternating current field directly in a flowing liquid, this results in that the flowing liquid itself forms ohmic resistance in the electrical current circuit by intense electron flow in the associated alternating current field. In practical embodiments, the flow of electrons through the liquid can be imposed, in an advantageous way, by the voltage, and with the current pulse, which is used in standard power line networks on land or onboard ships when needed.

Alternating current can possibly be supplied from the network on land, with alternation between plus and minus in a sequence of 60 periods per second, as this is common. But it is also possible, for example onboard a ship, to use transformers that give a much higher or much lower number of current pulses per second in cases where this should be relevant. In that the electron flow occurs "the shortest route" between two conductors, the alternating current fields are correspondingly limited to a relatively limited area, but still with sufficient current intensity for the entire cross section of the flow of liquid to be covered by the alternating current field and alternating current fields, respectively. This results in that the flow of electrons through the flow of liquid can be limited to the extent of the area that is covered by the associated alternating current field.

One, two or several alternating current fields, respectively, arranged in a row in the passage through the treatment component can be used in the passage according to need.

The alternating current fields ensure that wandering of electrons between the conductors propagates with enormous speed in relation to the optimal, yet relatively low, flow velocity of the water flow. In all cases, it will be possible to ensure that the water flow, even at optimal velocity, is time-wise ensured effective electron radiation across the running alternating current field.

Instead of using regular current pulses with 60 periods per second, much higher period numbers can alternatively be used, thus to ensure a denser electron radiation of the flow of liquid.

It is normally considered that one should avoid any use of alternating current, both at high and low voltages, in direct connection with water or similar liquids. It is normally regarded that one should especially avoid the use of alternating current in connection with a flowing liquid, particularly to prevent that the alternating current shall spread to the surroundings in an uncontrolled and hazardous manner with the help of the flow of liquid. Therefore, it has not been obvious to attempt treatment of a flowing liquid with alternating current effects.

It is on this basis, surprising that one according to the invention, in an easy, straightforward, and above all, safe way, can treat a flowing liquid in a controlled manner with one or more alternating current fields that are arranged across the flow path of the liquid.

According to the invention, one can consequently instantaneously destroy organisms that are present in the flow of liquid itself, by electron radiation of the organisms without this creating problems in the surroundings of the treatment installation.

In general, it can be relevant to use one-phase or three-phase alternating current or zero point alternating current, according to the actual conditions at the place of application and then with different amperage, different voltage and different frequency, according to need. Alternating current with different frequency can be used, for example, according to need and availability, with the help of a pulse generator or an alternating current converter. Actual amperage can easily be regulated with standard resistance regulation according to need.

Experiments have shown that the method, where this is relevant, can, for example, be used in a continuous way or divided into sequences according to need. The method can, for example, be used in connection with a continuous liquid flow in a single through-flow through the treatment installation, such as in handling of ballast water. Alternatively, the treatment can be performed over a limited time period. In all cases, the treatment can be performed with an optimal result without detectable negative consequences.

It is also possible, according to the invention, to use a treatment of a liquid while the liquid is in a tank or in a different storage arrangement. This can be ensured by subjecting the liquid to a local electrical effect in the treatment installation itself by recirculation of the liquid via the treatment installation from and to the storage appliance, as the liquid is led in a forced liquid flow through the treatment installation, separate from the storage arrangement.

According to another aspect, the present invention relates to an installation for treatment of a liquid that contains live organisms, comprising a treatment component in a treatment installation, where the treatment component comprises devices for handling of the fluid and also devices for destruction of live organisms in the liquid.

According to the invention, the installation is characterised by the combination of first devices to guide the liquid in a forced flow movement in an internal passage through the treatment component, and by second devices for subjecting the live organisms in the flow of liquid to an electron radiation in the internal passage in the treatment component.

According to the invention, the installation is further characterised in that the devices to subject live organisms in a flow of liquid to an electron radiation comprise conductors that are localised internally in the internal passage in the treatment component and which are arranged in a plane across the flow of liquid for the formation of an alternating current field with electron radiation of the flow of liquid in the cross section of the flow in the passage.

Further, the installation is characterised in that at least two conductors, being connected to a source for alternating current for activation of at least one alternating current field in the flow of liquid, are arranged internally in the pipe-formed passage.

The installation is also characterised in that the conductors are arranged at a mutual distance which ensures that the flow of liquid through the pipe-formed passage is activated by the alternating current field in the whole cross section of the passage, and that the pipe-formed passage is surrounded by a case of electrically insulating material, and also that an activated alternating current field is locally limited in its entirety within the axial extension of the passage.

The installation according to the invention has been tested in practice for use with various flow amounts and for use with different types of water, i.e. both seawater and polluted fresh water (river water in city environments) and also drainage water or sewage, with use of relatively simple components in the treatment installation. The water that flowed through the treatment installation was, in certain tests, subjected to high pump power in connection with a supply pipe with a cross section corresponding to that used for filling of ballast water in the ballast tanks onboard ships and for emptying of ballast water from ballast tanks onboard ships. In other tests, the water was subjected to a lower pressure force and subjected to lower flow velocity, respectively, in the treatment installation by application of the height of fall of water as pressure force.

Tests performed with water that was treated in the installation according to the invention, have, in different tests, given convincing positive results both with regard to complete destruction of all kinds of organisms and with regard to controlled protection against spreading of electrical current with regard to the surroundings of the installation.

Further, the present invention relates to a treatment component for use in an installation for treatment of a liquid containing live organisms, where the treatment component comprises devices for handling of the liquid and also devices for destruction of live organisms in the liquid.

The treatment component, according to the invention, is characterised in that by the combination of first devices to guide the liquid in a forced flow movement in an internal passage through the treatment component, and by second devices to subject the live organisms in the flow of liquid to an electron radiation in the internal passage in the treatment component.

The component has the advantage that it can be incorporated in a simple and easy way according to need as an easily replaceable unit in existing pipeline systems in actual treatment installations as an easily replaceable unit in new pipeline systems, respectively.

In this context, the component is characterised in that it contains a pipe bundle which is replaceably fitted with relation to the rest of the treatment installation, and that the pipe bundle comprises a number of passages mutually running in parallel where each is surrounded and is limited by an electrically insulating, pipe-formed case.

The mentioned component can be used as special equipment connected to different apparatuses for industrial use, for use in hospitals, for use in bathing installations, in swimming halls, in hotels or other arbitrary locations by adapting the components to different types of pipe systems and so on, i.e. comprising adapting to one or several parallel running components of the pipeline system, according to need.

The component, according to the invention, is further characterised in that this component, which constitutes a main component, is streamwise connected upstream to at least one additional component that is set up for mechanical crushing of macroorganisms, and that the additional component is arranged upstream and downstream, respectively, of the main component, and also that the flow of liquid from and to, respectively, the additional component communicates directly with the main component.

With the help of the main component in direct flow connection upstream of a crusher-forming component, it is possible to start destruction of macroorganisms by mechanically dividing up these macroorganisms immediately before a subsequent treatment of the liquid with an alternating current field in the main component. By arranging of a such additional component downstream of the main component, destroyed macroorganisms can be further divided up, and/or according to need, be removed separately from the flow liquid. With the help of such a close connection of the mentioned component, one can immediately after the first mentioned crushing of the macroorganisms, ensure a subsequent, effective and instantaneous destruction and possibly further division of macroorganisms, and also filter and remove remains of destroyed organisms.

Further features of the invention will appear in the following description which describes preferred solutions. However, the invention is not limited to the mentioned preferred solutions, as the invention can have corresponding effect in connection with other problems to be addressed and other objectives. The following description refers to the enclosed drawings in which:

FIGS. 1a and 1b show schematically a side elevation and a cross section, respectively, of an actual arrangement of ballast tanks onboard a bulk ship.

Figure 1:
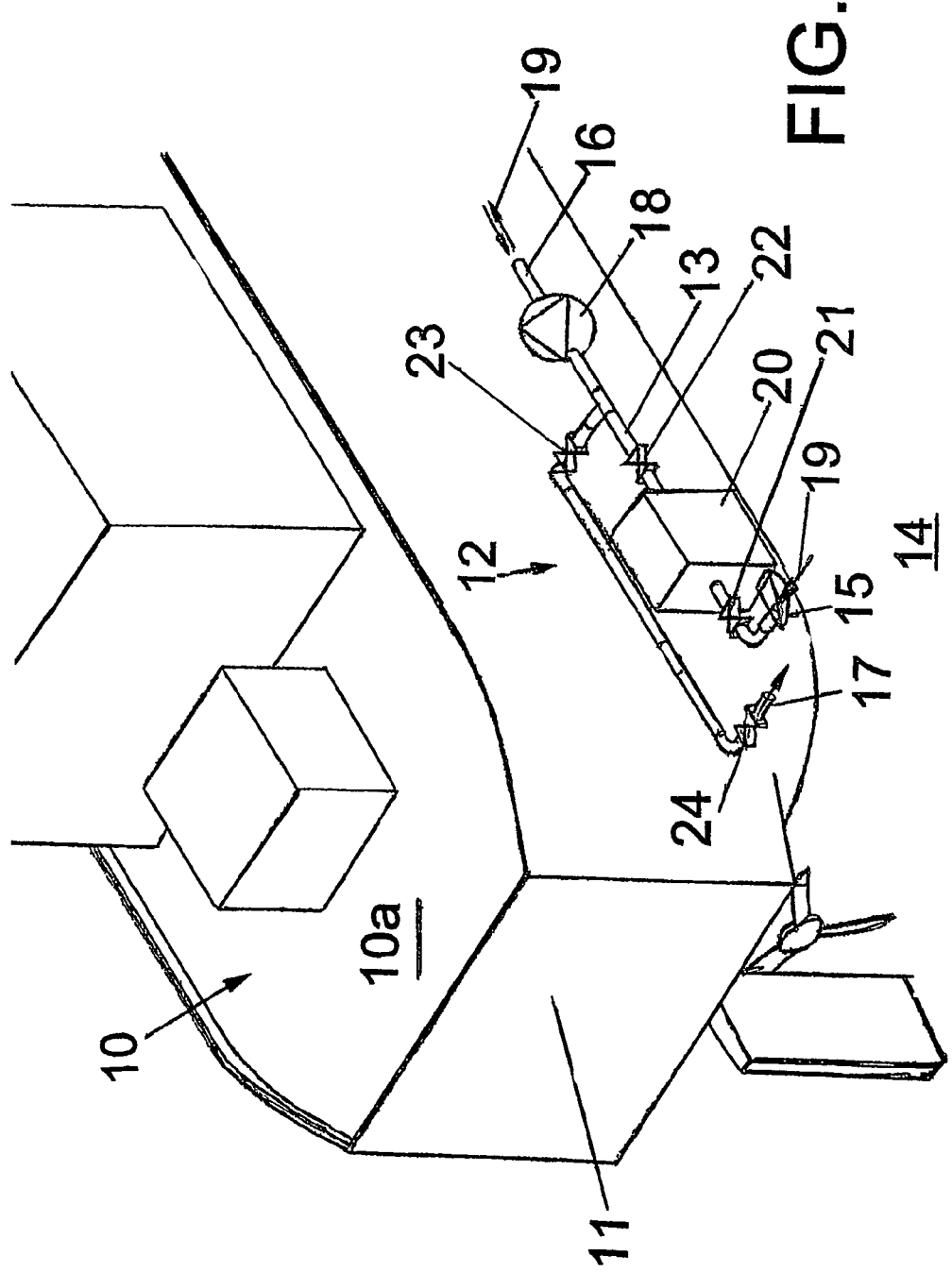
FIG. 1 shows schematically a section of a ship that is equipped with an, per se, installation for handling of ballast water, i.e. in filling of ballast water onboard the ship and in emptying of ballast water from the ship, respectively.

FIG. 1 shows a section of a ship 10 which is shown with its stern 11. A section of a standard, in itself known, ballast handling installation 12 for handling of ballast water in a pipe system 13 corresponding to that used onboard bulk ships tankers and similar cargo ships, is shown schematically.

Ballast water is filled from the harbour area in a first harbour from the sea side 14 of the ship 10 via a water inlet 15 to a number of mutually separate ballast tanks 10*b* (see FIGS. 1*a* and 1*b*), which, in a way not shown in detail, are connected to the shown inner end 16 of the pipe system 13. In a subsequent harbour, the ballast water is emptied from the ballast tanks 10*b* via a water outlet 17 back to the sea side 14 in the new harbour area.

The installation 12 is equipped with a water pump 18 that is placed downstream just by the shown inner end 16 of the pipe system 13. During the filling process, the pump 18 can suck seawater from the sea side 14 via the water inlet 15 and deliver the water further as ballast water to the different ballast tanks 10*b* of the ship in turn via the pipe system 13 in a direction which is indicated by arrows 19. A seawater filter 20 is inserted in the pipe system 13 downstream, immediately inside the water inlet 15 to prevent that macroorganisms, such as fish, shellfish and so on, shall be transported together with the water stream further into the ballast tanks 10*b*.

A first valve 21 that can be remotely controlled, for opening and closing of the pipe system 13 towards the sea side 14, is inserted between the seawater filter 20 and the water inlet 15. A second valve 22 that can be operated remotely controlled for opening and closing of the pipe system 13 between the filter 20 and the pump 18, is inserted downstream just behind the filter 20. Both valves are put in an open position during filling of ballast water, while they otherwise take up a closed position to prevent unintentional flow of water into and out of the installation 12.

During the emptying process, the water pump 18 sucks ballast water via a pipe 23 from the ballast tanks 10*b* and empties the water out again to the sea side 14 of the ship 10 at the water outlet 17. It is ensured that remotely controlled valves 23, 24 can be placed in an open position so that the flow of water can be led through the pipe 23 in the pipe system 13 in a direction as shown by the arrow 19*a* towards the water outlet 17. The flow of liquid through the pump 18 can be reversed in mutually opposite direction when needed, while the flow of liquid through the ballast handling installation 12 can correspondingly be controlled in mutually opposite directions when needed by a corresponding remote control of the valves 21, 22 and 23, 24, respectively.

A side section of a bulk ship of a size of about 400,000 dwt. with a load capacity for ballast water of about 160,000 tonnes is shown schematically in FIG. 1*a*.

A cross section through the middle cargo room 10*a* of the ship 10 and its adjoining ballast room 10*b* on the opposite sides of the ship 10 is shown in FIG. 1*b*. The ballast rooms 10*b* on each side of the ship can, for example, be arranged in a number of eight mutually separate tank units 1*b*' which are arranged in a row in the longitudinal direction of the ship 10 as shown schematically in FIG. 1*a*. Each unit 1*b*' can further be divided up into five mutually communicating sections 1*b*'' which are mutually connected via cut-outs 1*b*''' as shown in FIG. 1*b*.

Figure 2:
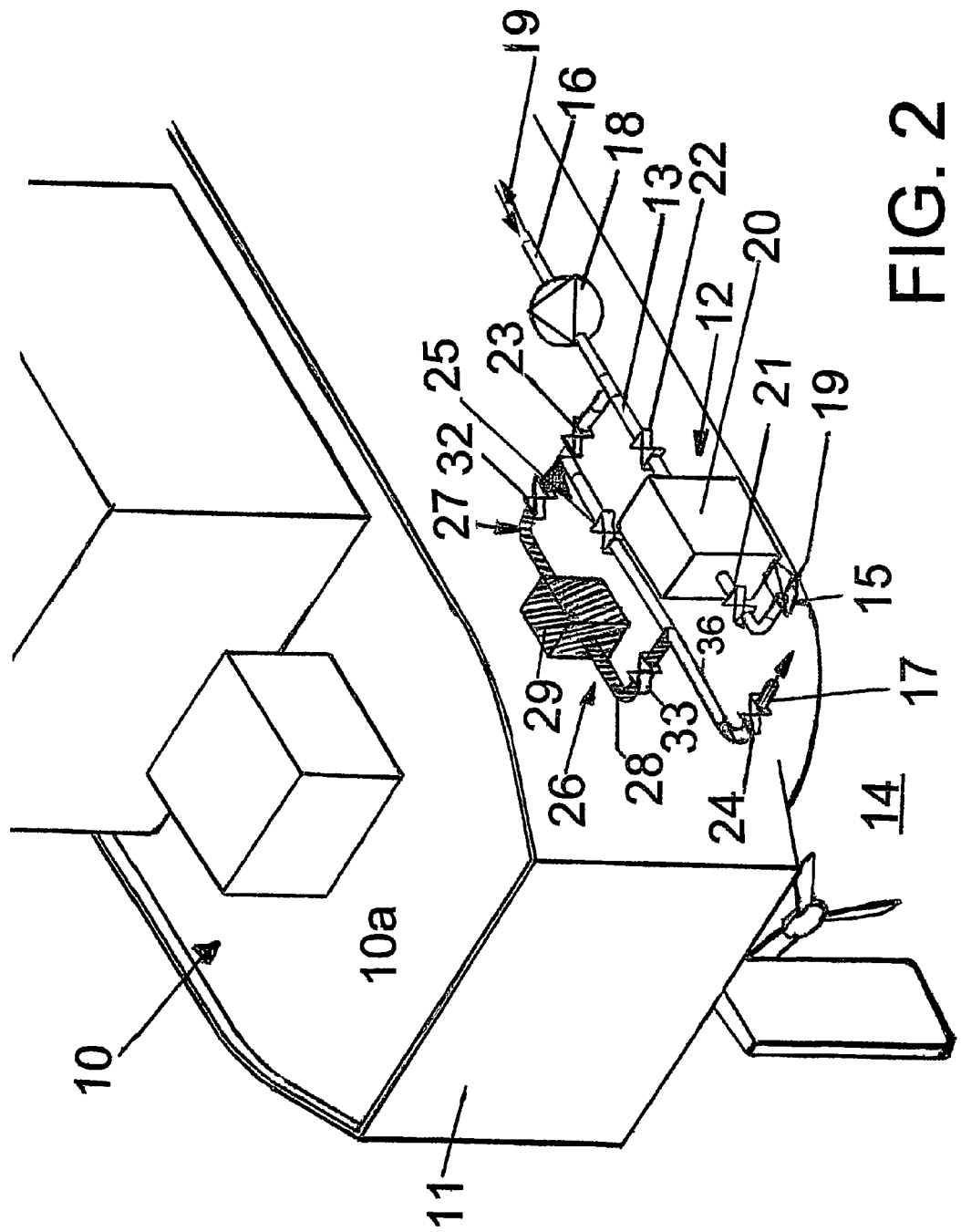
FIG. 2 shows schematically a section of a treatment installation according to the invention, where the treatment installation is fitted in its entirety onboard a ship and where it is shown fitted in connection to an, in itself known, ballast handling installation as shown according to FIG. 1.

A treatment installation 26 according to the invention is shown in FIG. 2. More accurately the treatment installation 26 constitutes a combination of a ballast handling installation 12, as shown in FIG. 1, and additional equipment 27 according to the invention.

The additional equipment 27 is marked on the drawing by shading to clarify.

The complete treatment installation 26 is, according to FIG. 2, arranged internally in the ship, as the additional equipment 27 is incorporated in direct connection to the existing ballast handling installation of the ship 10 with associated pipe system 13 and other associated equipment. Consequently, other existing equipment onboard the ship can be utilised, i.e. pump 18 with existing remote control system and valves 21-24 with associated remote control system for operation of the treatment installation 26 according to the invention.

In addition, according to the invention, one has as additional equipment arranged a further remote controlled valve 25 in the pipe system 13 between the valves 23 and 24.

According to the invention, one has as an additional advantage the possibility of using the electricity generator of the ship for supply of electrical energy for use in the treatment installation 26 according to the invention. Furthermore, one has the possibility to use the same electrical energy source both in the ballast handling installation 12 and in the treatment installation 26 according to the invention.

Figure 5:
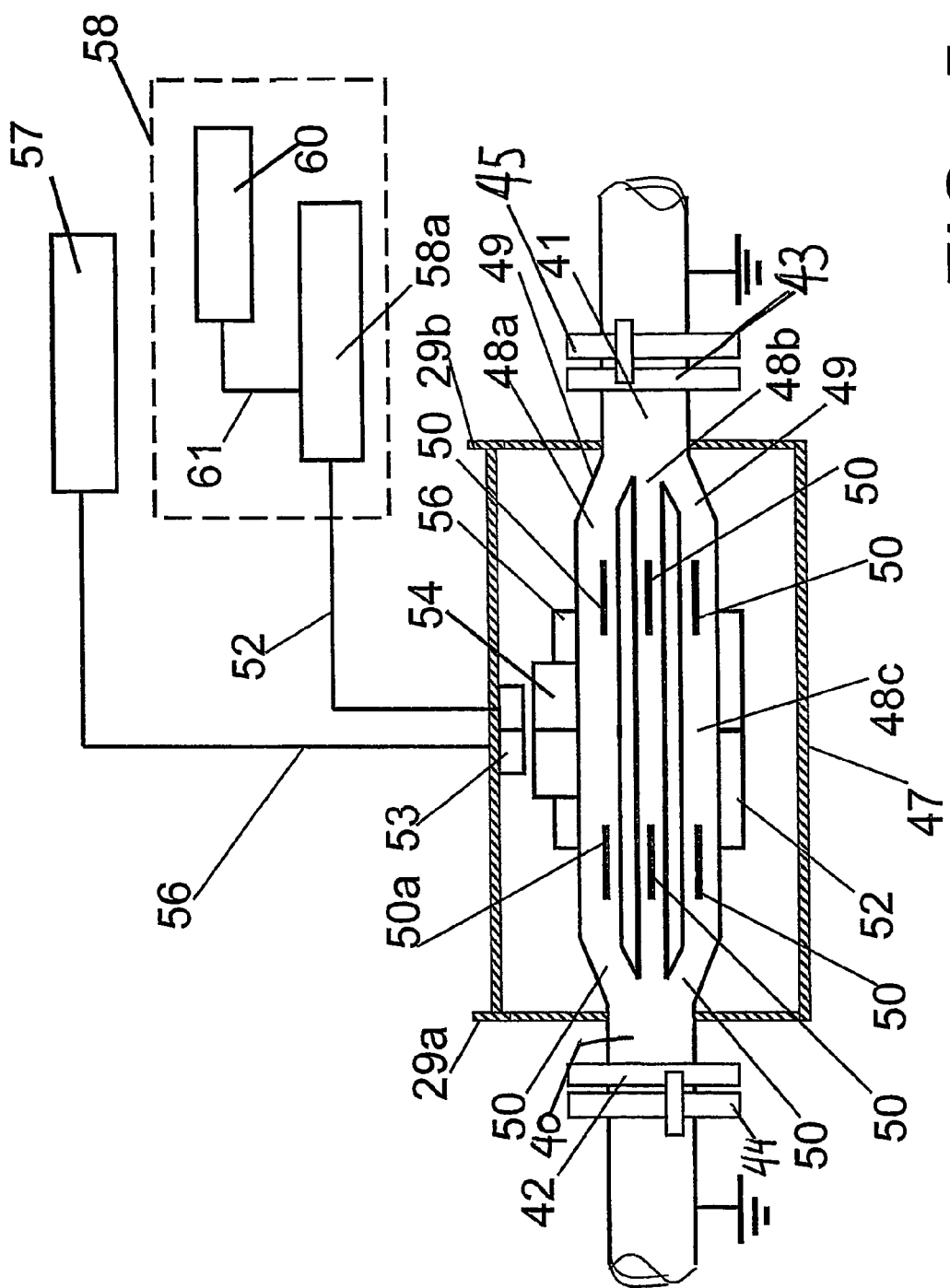
FIG. 5 shows a component according to the invention that is part of a main component in the treatment installations that are shown in FIGS. 2, 3 and 4 and the subsequent FIGS. 12 and 13, respectively.

The additional equipment 27 comprises, according to the embodiment in FIG. 2, in addition to the valve 25, a pipeline 28 that comprises a treatment component 29, which is shown in detail in FIG. 5, and also two remote controlled valves 32, 33. The pipeline 28 with the treatment component 29 is used in the embodiment example shown for treatment of ballast water that shall be emptied from the ballast tanks 1*b*, with the pipeline 28 being connected to the pipe system 13 via open valves 23, 32, 33, 34 as the other valves 21, 22 and 25 take up a closed position.

A pipeline 36 is limited in the pipe system 13 directly between the pump 18 and the outlet 17, at the opening of the valve 24 and closing of the valves 21,22 and 32,33. The pipeline 36 runs directly between the pump 18 and the outlet 17 and is used for handling of ballast water in an emergency situation, as the pipeline 36 bypasses the treatment installation 26 according to the invention.

Figure 3:
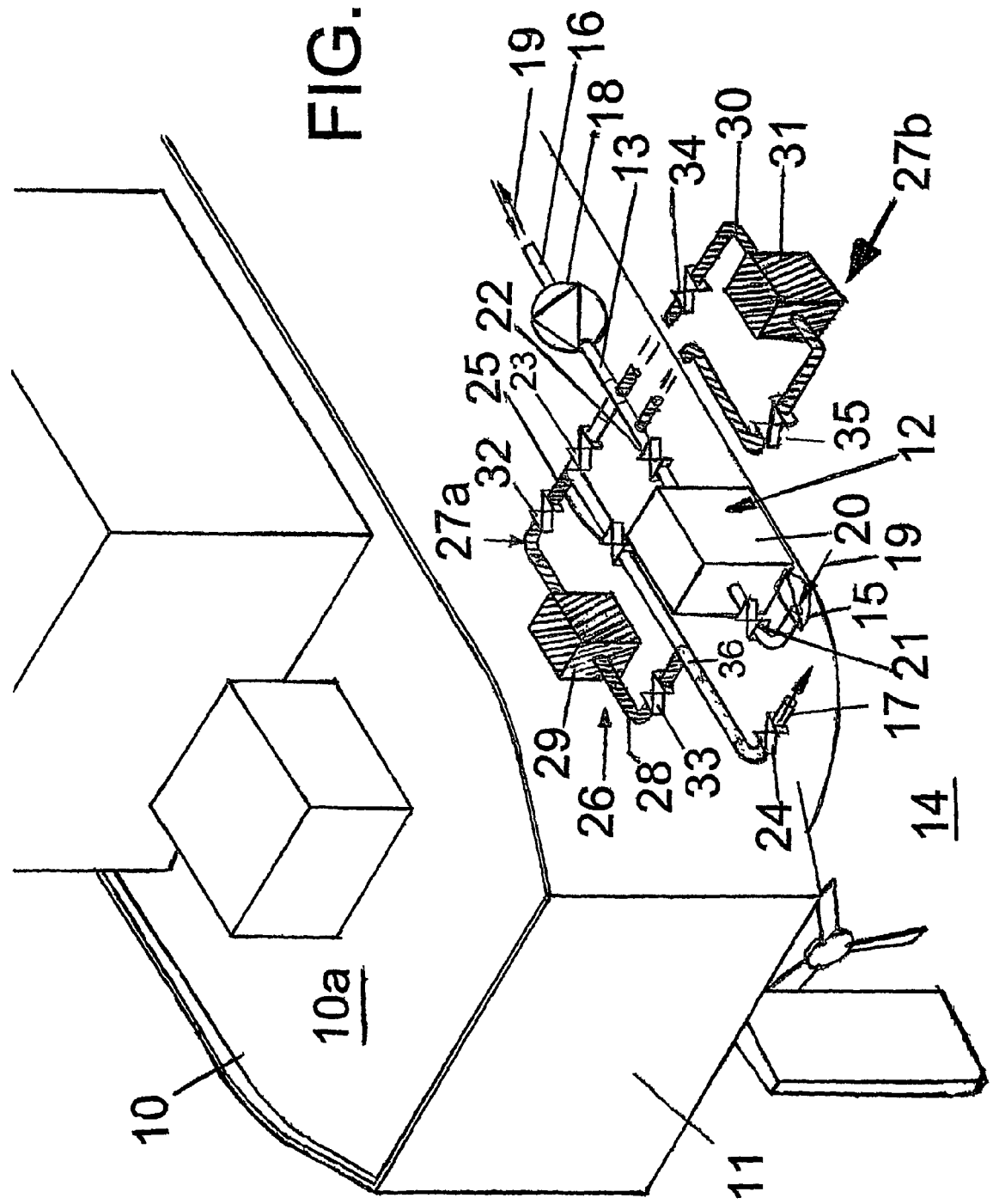
FIG. 3 shows schematically a section of an alternative arrangement of the treatment installation as shown in FIG. 2.

The additional equipment 27 as it is shown in an alternative treatment installation in FIG. 3, comprises a combination of two mutually separate units 27*a* and 27*b* which each is marked by shading in the drawing.

In addition to a first unit 27*a* with a first pipeline 28 and a first treatment component 29, as shown in FIG. 2, a corresponding second unit 27*b* is applied with a second pipeline 30 that comprises a second treatment component 31.

The first pipeline 28 with the first treatment component 29 is used for treatment of water that is emptied from the ballast tanks 1*b*, corresponding to what is shown in FIG. 2, while the second pipeline 30 with the second treatment component 31 is used for treatment of water that is filled from the sea side 14 via the pipe system 13 to the ballast tanks 1*b*.

The pipeline 28 is also, according to FIG. 3, connected to the pipe system 13 via remote control valves 32, 33, while the pipeline 30 is connected to the pipe system via corresponding remote control valves 34, 35. A pipeline 36 also runs in the pipe system 13 directly between the pump 18 and the outlet 17 for handling of ballast water in an emergency situation. Consequently, the treatment installation 26 can be connected to and disconnected from the ballast handling installation 12 according to need, by correspondingly closing and opening, respectively, of the valves 23, 24.

According to FIG. 3, the treatment installation 26, which comprises two separate units 27*a* and 27*b*, can consequently be used both during filling and emptying of ballast water or if so desired, only during filling or only during emptying via the different units 27*a* and 27*b*.

The embodiments shown in FIGS. 2 and 3 have the objective that the treatment installation 26, which is placed onboard the ship 10 in its entirety, is handled by the people in charge onboard the ship 10.

Figure 4:
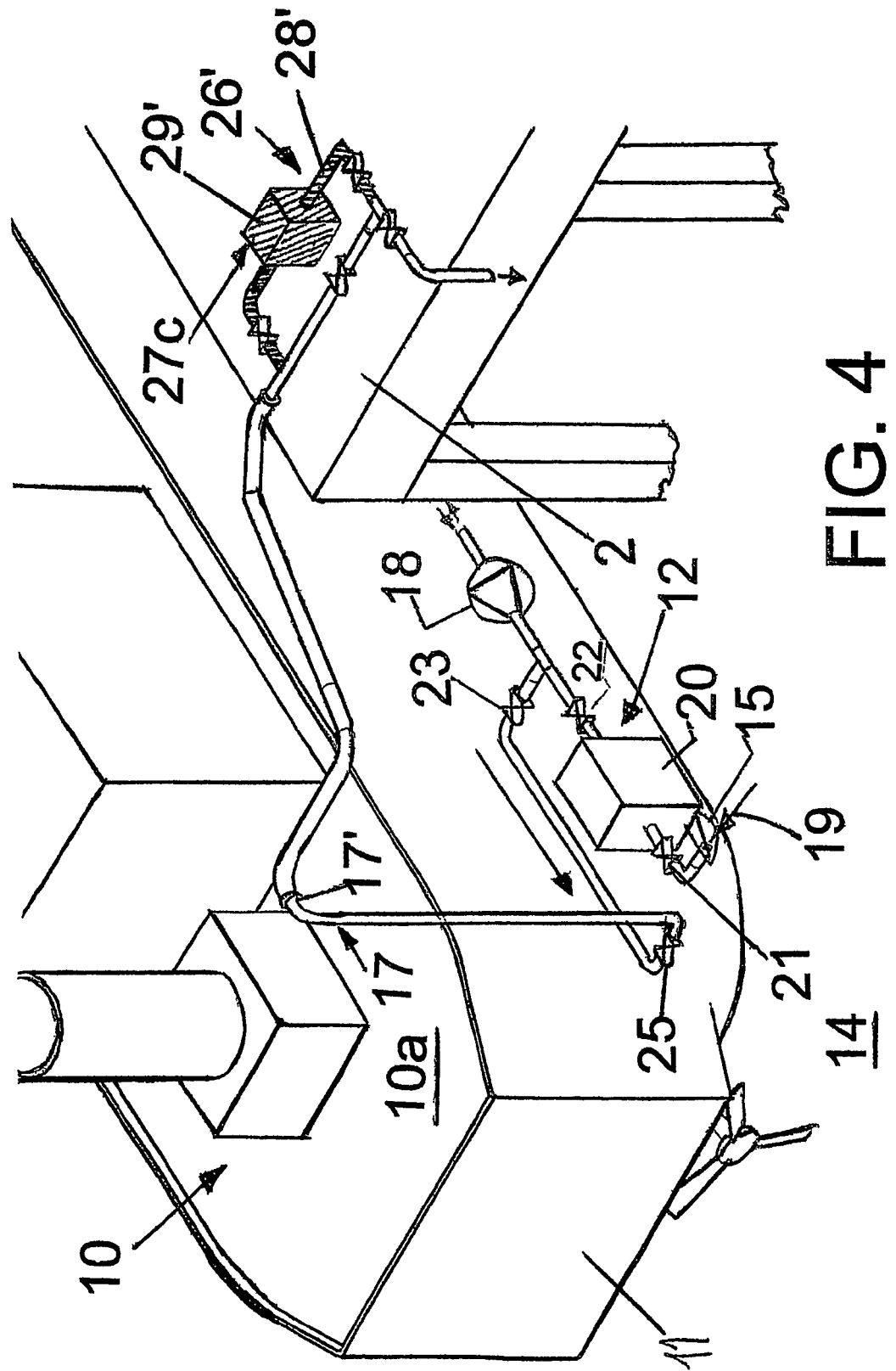
FIG. 4 shows schematically a section of a treatment installation according to the invention where essential parts of the treatment installation are arranged on a quayside outside the ship.

A third solution for the treatment installation 26 according to the invention is shown in FIG. 4, where the unit 27 is placed on a quayside 2, i.e. placed apart from the ship 10. In this embodiment example the treatment installation 26 and/or the unit 27 can, for example, be handled by the people in charge at the loading location or the unloading location, for example, by local harbour authorities, as these can possibly themselves control the operation of the treatment installation 26 via their own control system and possibly their own electricity supply.

The advantage with a locally arranged treatment installation 26 is that different ships can in turn be treated with one and the same treatment installation. The loading and unloading operations themselves can be performed with the ballast handling installation onboard each ship with the help of the ballast handling installation 12 and with the help of the people in charge onboard the ship.

According to FIG. 4, the outlet 17 from the ballast handling installation 12 of the ship 10 is shown with a flanged pipe end 17', that extends upwards to a suitable height above the deck 10a of the ship 10. The flanged pipe end 17' is shown in FIG. 4 connected to additional equipment 27c in the form of a pipeline 28' with associated treatment component 29'. According to FIG. 4, the treatment installation 26 can be combined with the ballast handling installation 12 onboard the ship in a correspondingly advantageous way as shown in FIGS. 2 and 3. Alternating current to the treatment component 29 can be supplied from the ship 10 or from the quayside 2, according to what is wished for or required, in a way not shown in any detail.

Alternatively, the additional equipment 27c can completely or partially be arranged outside the ship 10, for example, arranged onboard a barge or another vessel brought along the side of the ship or arranged in a hanging position at the side of the ship without this being shown in any detail herein. The treatment installation 26 can, in such cases, be handled outside the ship by the harbour authorities or other responsible bodies in the harbour area.

A vital component 29 in the treatment installation 26 is shown in FIG. 5. The component 29 constitutes an easily replaceable pipe-formed unit with two opposite pipe-formed sections 40, 41 with associated fastening flanges 42, 43 that are adapted for simple, replaceable connection to fastening flanges 44, 45 in a pipeline 28 according to FIG. 2 and in a pipeline 30 according to FIG. 3, respectively, or in a pipeline 28' according to FIG. 4 as required.

The flanges 42-43 and 44-45, respectively, are equipped with corresponding grooves 46 (see FIG. 9) in the circumference area for correct positioning with the help of guiding pins 47, which ensure that the component 29 is mounted at an accurately adjusted angle position in relation to associated pipeline 28, 30 and 28', respectively. The component 29 is equipped with lifting hooks 29a and 29b for ease of fitting to and dismantling from the pipe system 13.

A pipe bundle of, for example, six pipe branches 48a, 48b, 48c, 48d, 48e, 48f (see FIGS. 6 and 7) is connected between the pipe-formed sections 40, 41 inside the shown coat 47 of the component 29, via adjacent guiding channels 49a. Only three of the mentioned six pipe branches are shown in FIG. 5 for clarity. In practice, the pipe bundle 48a-48f can comprise, for example, two separate pipe bundle parts 48a-48c, and 48d-48f. It is made sure that the pipe bundle of six pipe branches or each pipe bundle part of three pipe branches can easily be fitted and dismantled in the inactive position of the coat 47 as shown in FIG. 7.

In the embodiment example shown, the pipe-formed sections 40 and 41 have an internal diameter corresponding to the cylindrical pipelines 28, 29. The corresponding cylindrical pipe branches 48a-48e have each a reduced internal diameter. The combined flow of liquid through the passage 49 in the pipe branches 48a-48e can, by and large, correspond to the flow of fluid in the sections 40 and 41, respectively. The combined flow cross section through the passage 49 in the pipe branches 48a-48e is preferably much larger than the flow cross section through the pipeline 28, and through the sections 40 and 41, respectively. The result is that one can achieve reduced flow velocity through the pipe branches thereby to extend the residence time of the liquid in the treatment component 26 itself.

Figure 9:
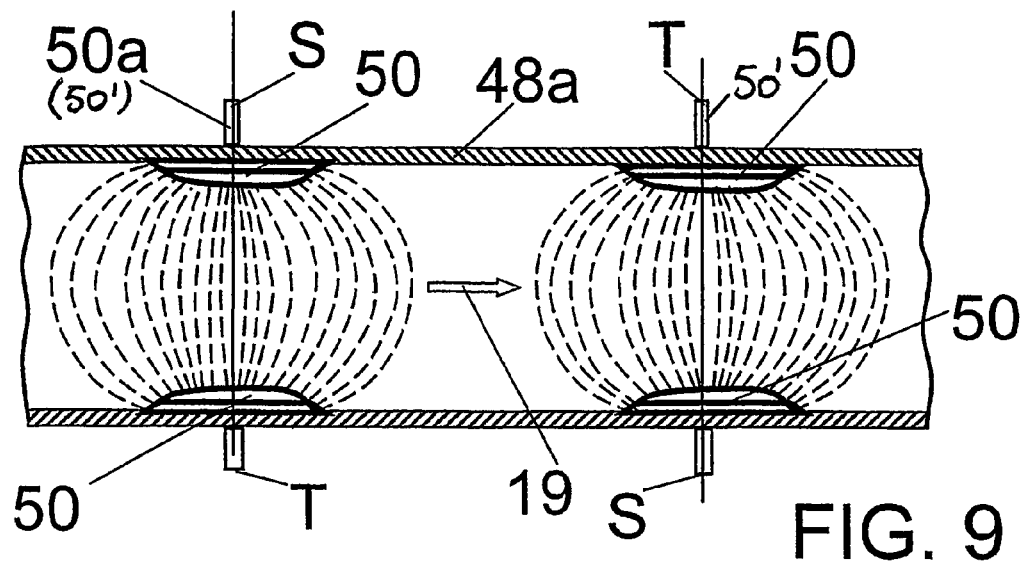
FIG. 9 shows in longitudinal section an alternative embodiment example of a pipe branch which is equipped with two pairs of conductors that form their own alternating current field across a liquid flow through the pipe branch, based on one-phase alternating current.

The passage 49 through each pipe branch 48a-48e is surrounded by an insulating case 48 which is manufactured from an electrically insulating material (plastic). A pair of conductors 50 arranged diametrically opposite each other are fastened at opposite ends on the inside of the case 48, as shown in FIG. 9. Fan-formed alternating current fields that radiate between each pair of electric conductors 50 are schematically indicated in the figures with dotted lines. The electric conductors 50 are connected to an alternating current source 58, i.e. onboard the ship 10 connected to a standard electric generator via a cable 52 for alternating current.

Figure 6:
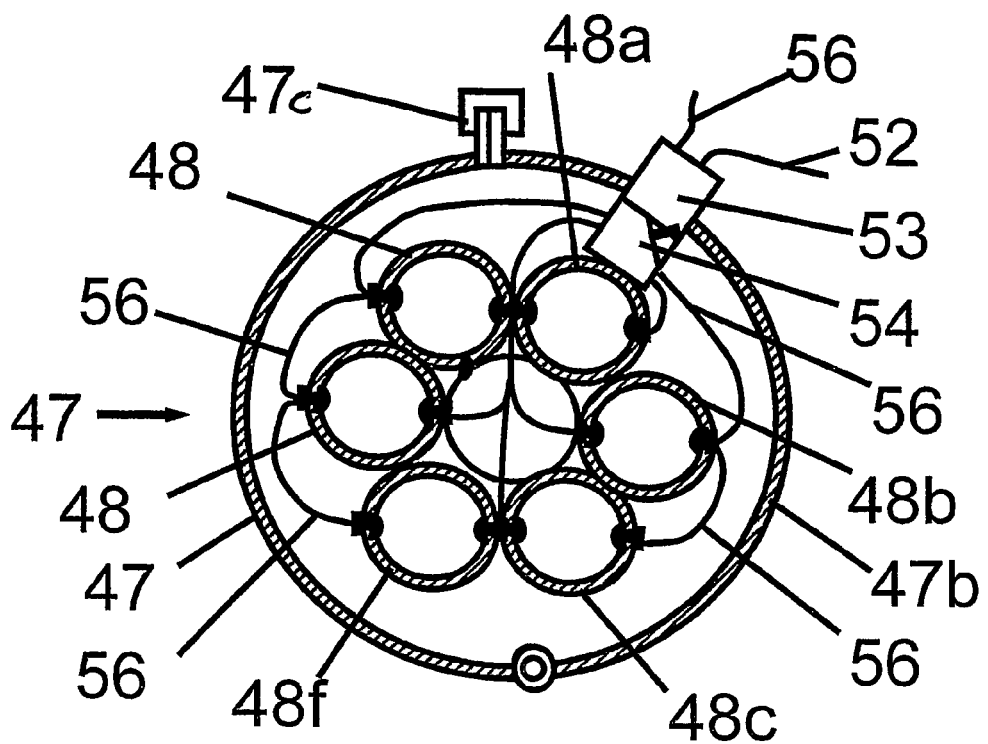
FIG. 6 shows a cross section of the component according to FIG. 5, shown in an active use position.
Figure 7:
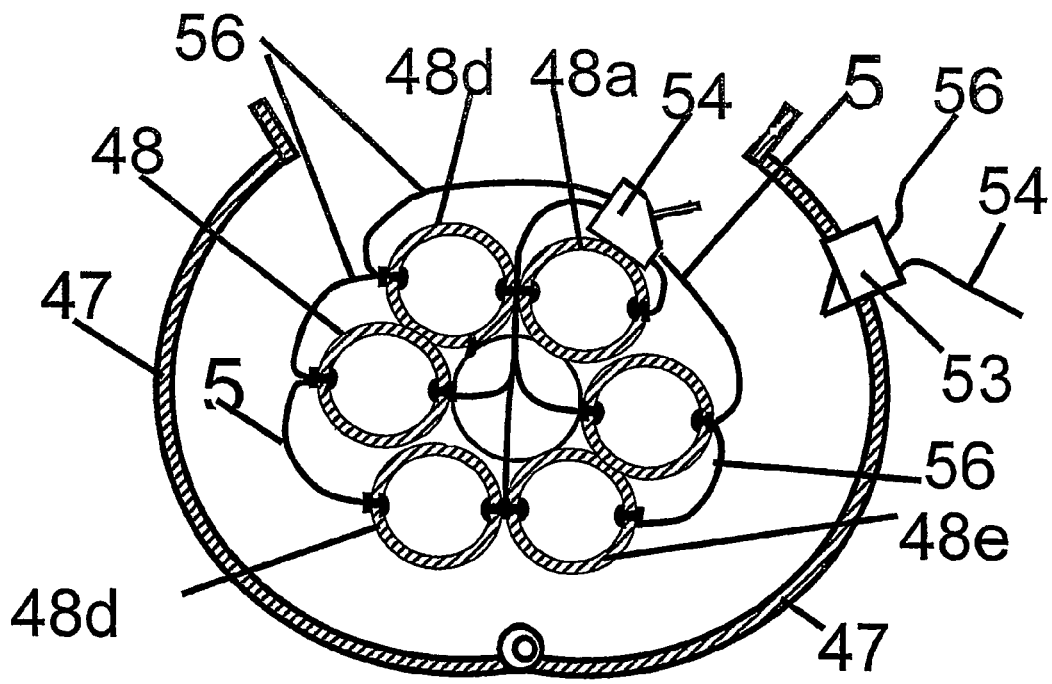
FIG. 7 shows a cross section of the component according to FIG. 5, shown in inactive position.

The cable 52 is, according to FIGS. 6 and 7, connected to a circuit breaker which is shown by a plug 53 that is fastened on the one half 47b of the coat 47, and a socket 54 which is fastened on the one pipe branch 48a.

The cable 52 extends from the socket 54 on the one pipe branch 48a to the electric conductors 50 of the different pipe branches 48a-48f. The cable 52 is connected with taps 50' that run through the pipe wall of the case 48 in a watertight and gas proof way in the extension of the associated electric conductor 50.

The coat 47 is, as shown in FIGS. 6 and 7, divided into two coat parts 47a and 47b hinged together at the bottom. The one revolvable coat part 47a carries the plug 53 and the one stationarily arranged pipe branch 48a carries the socket 54. The coat parts 47a and 47b are revolvable toward each other from an inactive position, as shown in FIG. 7, to an active use position, as shown in FIG. 6, while the plug 53 and socket 54 of the circuit breaker are activated for current transmission simultaneously. In a position revolved together, the plug 53 and the socket 54 are locked together in active engagement by locking the coat part 47a and 47b with a locking part 47c, as shown in FIG. 6.

Figure 8:
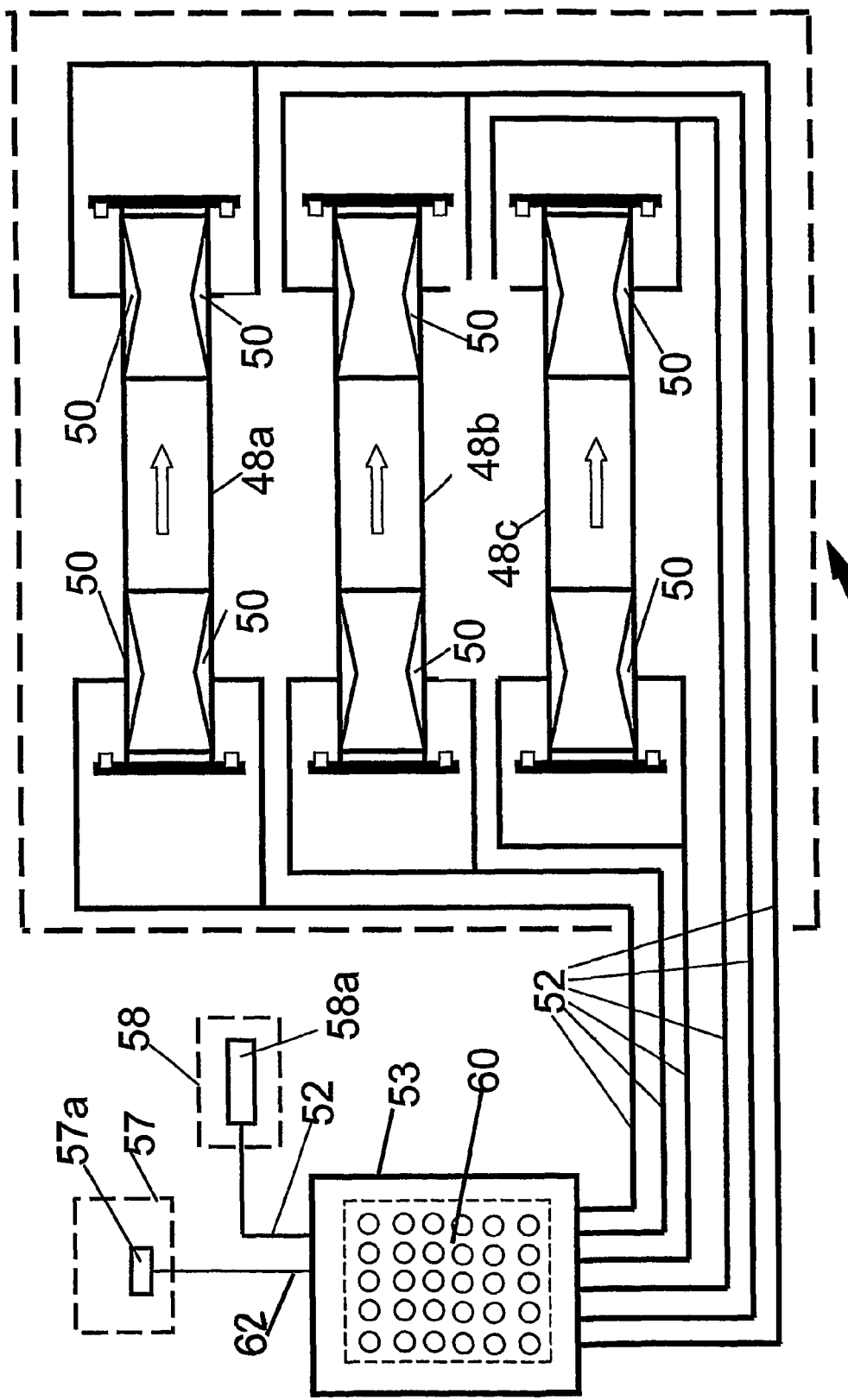
FIG. 8 shows three pipe branches in longitudinal section, that are part of the component according to FIG. 5 and each of which is equipped with two pairs of electric conductors which in the axial direction form their own axially limited alternating current field in a liquid flow through the pipe branch, based on one-phase alternating current.

A low current cable 62 that forms a connection between the plug 53 and a schematically indicated guiding equipment 57a placed on the bridge 57 of the ship 10 is shown in FIG. 8, as the low voltage guiding current guides the activation of and deactivation of the plug 53. The main current to the plug 53 via the cable 52 is supplied from a current aggregate 58a or a dynamo in the engine room 58 of the ship 10. The main current in the cable 52 can be connected to and disconnected from the treatment installation 52 when needed via the mentioned guiding equipment 57a on the bridge of the ship or a corresponding, not shown in detail, guiding equipment in the machine room 58 of the ship 10.

A schematically drawn control panel 60 is shown in FIG. 8 with associated cable connection to each of the electric conductors 50 in each of the pipe branches 48a-48f. Only three of the pipe branches 48a-48c are shown in the drawing. With the help of the control panel 60 and associated cable connections, alternating current of different types i.e. one-phase, three-phase or zero-point alternating current, can be imposed from the machine room 58 according to need, as all these various types of alternating current are available from the electricity generator of the ship. The different electric circuits, R, T, S that are shown in FIG. 8 relate especially to three-phase alternating current, as the different phases alternate between the two shown electric circuits with a frequency of 50 Hz.

The amperage to the electric conductors 50 in each pipe branch can, in an itself known way, be regulated according to need and can, for example, be set at a level of about 25 A. The voltage can correspondingly be set at different levels according to need, for example, to 110 V, 220 V, 380 V and so on. In addition, electricity can be supplied at different frequencies, for example, at 50 Hz or much lower or much higher, according to the type of alternating current that is chosen in the treatment installation, i.e. one-phase, three-phase or zero-point alternating current.

Figure 9A:
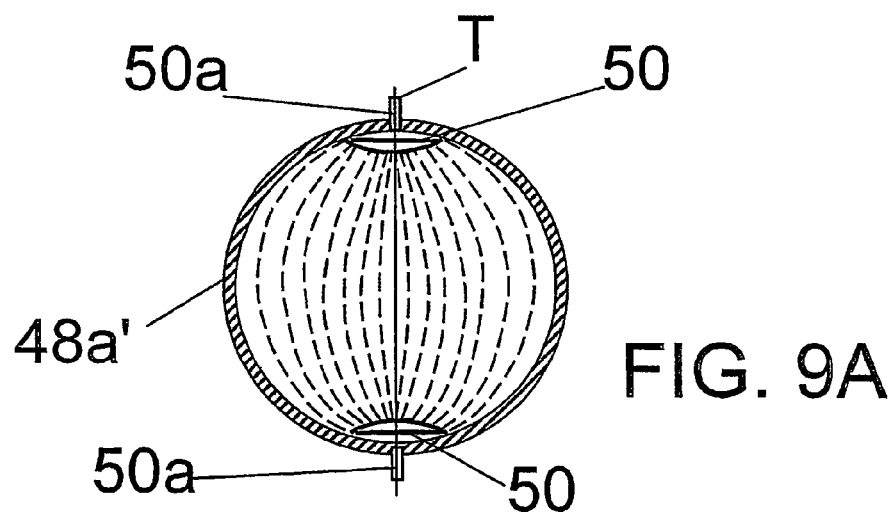
FIG. 9a shows the pipe branch according to FIG. 9 shown in cross section with the pipe branch being equipped with three electric conductors that form alternating current fields across a liquid flow through the pipe branch, based on three-phase alternating current.

Two pairs of electric conductors are shown in longitudinal section in FIG. 9 at each end of a pipe branch 48a. Tap-formed extensions 50a of the electric conductors 50 are shown, which extend straight through the wall of the case 48 to connect with each separate branch from the associated cable 52. Shown in FIG. 9a is a cross section of the pipe branch 48a in FIG. 9, with the cross section being shown in a section close by the one pair of electric conductors 50. A one-phase alternating current is used in each pair of electric conductors.

FIGS. 9 and 9a show, in addition, a preferred form of the electric conductors 50. The electric conductors are shown convex arched on their rear side corresponding to the internal curvature of the case 48, and shown to have a longitudinal and transverse arched, streamlined form on the opposite side. Both the tap-formed extensions 50a and the electric conductors 50 themselves are, in addition, surface treated with a gold covering on the associated outer surfaces. The alternating current fields are indicated with dotted lines between the respective electric conductors 50. An arrow 19' shows the direction of movement of the flow of liquid in the case 48.

Figure 10:
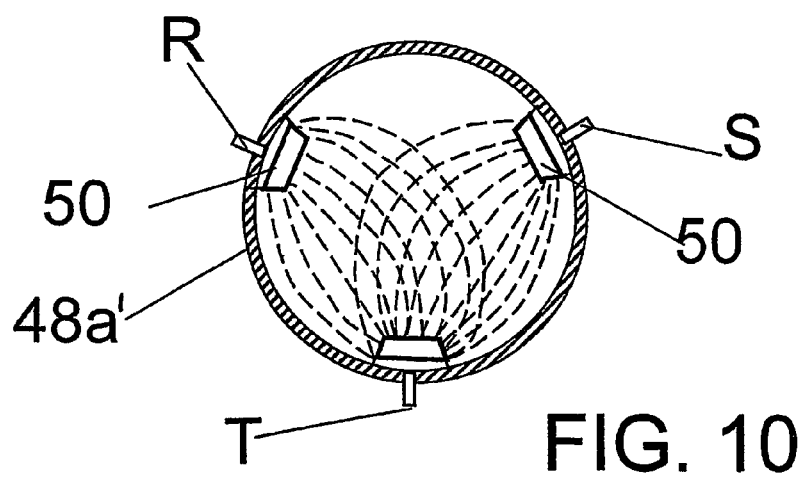
FIG. 10 shows in cross section an alternative embodiment example of the pipe branch according to FIG. 9.

A cross section of a pipe branch 48a', is shown in FIG. 10, equipped with three electric conductors 50 being arranged in a triangular-shape in a plane across the flow path through the pipe branch 48a. The electric conductors are shown with a circular disc-form and are shown to have a convex arch-shaped rear side corresponding to the internal curvature of the case 48 and on the opposite side shown with a plane top surface and two side surfaces slanting outwards. Two of the alternating current fields between the electric conductors are indicated with dotted lines.

Figure 11:
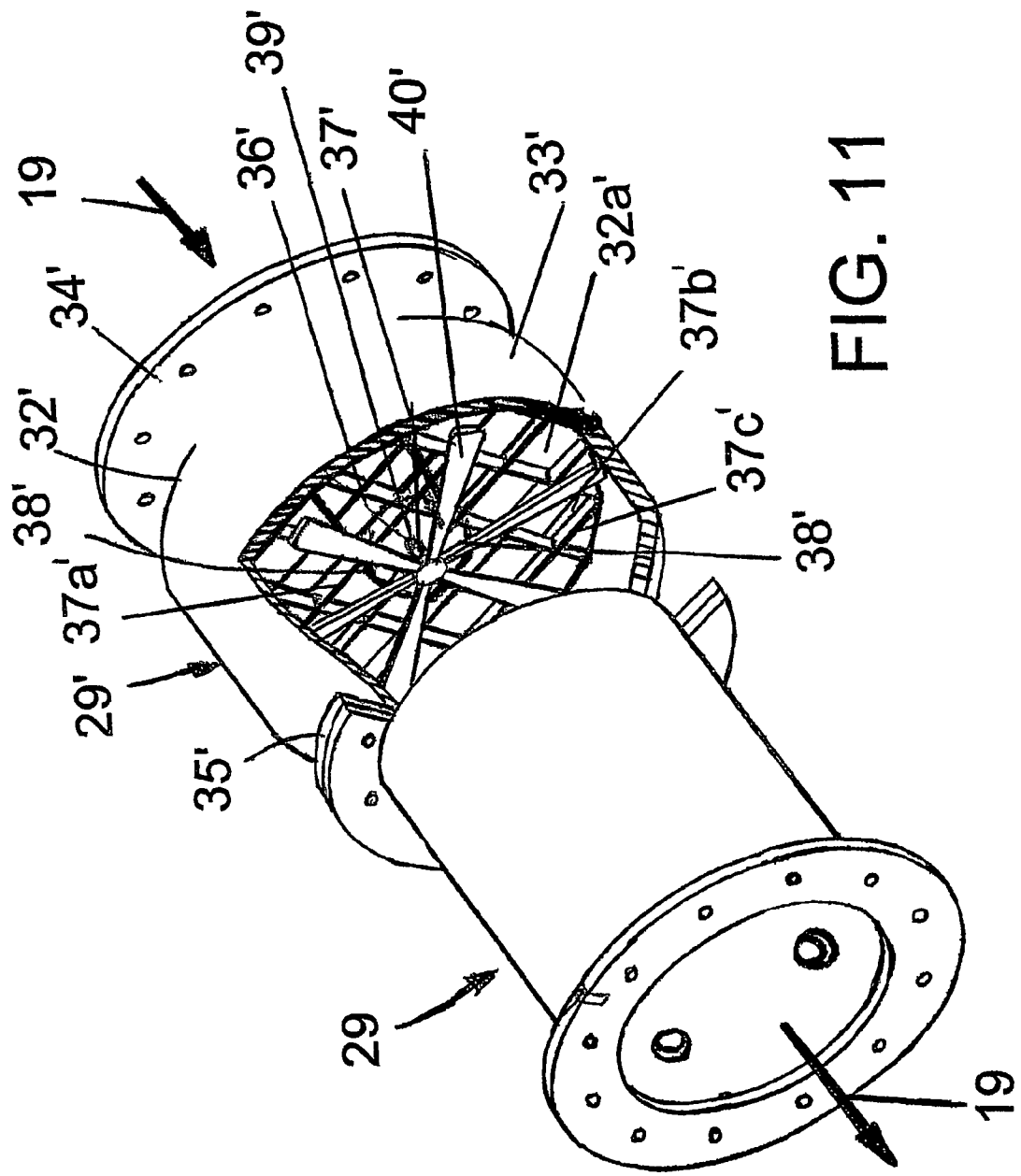
FIG. 11 shows an additional component that aims to crush live macroorganisms in the flow of water which is led through the treatment installation and which is placed at the upstream end of the main component of the treatment installation.

The treatment component 29 is shown schematically in FIG. 11 as a main component, which is connected upstream to an additional component 29' with direct, flow-wise connection between the components 29, 29'. Practically, the components 29, 29' can be handled as a joined unit, but with the possibility for easy disconnection of the additional component 29' from the main component 29 according to need.

The additional component 29' comprises a piece of pipe 32' which, in a cross section-wise radially expanded area 33' between associated fastening flanges 34' and 35', is equipped with two separate insert parts 36' and 37'.

The insert part 36' forms a combined grid and stationary crusher and is arranged upstream of the insert part 37', which forms a rotating crusher-knife.

The insert part 37' is shown in FIG. 9 in the form of a drive motor 38' with a drive shaft 39' of a multi-bladed, rotary crusher-knife 40'. The drive motor 38' is shown in the drawing arranged upstream of the one side of the insert part 37', while the crusher-knife 40' is arranged downstream on the opposite side of the insert part 37' and relatively close to the same insert part 37'.

Alternatively, the drive motor 38' can be arranged downstream in relation to the insert part 37'. The drive motor 38' fills up part of the cross section of the passage 32a' through the pipe piece 32' so that the remaining cross section corresponds or approximately corresponds in area to the flow cross section through the cross section of the additional component 29' at its opposite ends, while the flow cross section at the grid-forming insert part 37' and at the crusher-knife 40' has a locally increased through-flow cross section.

The drive shaft 39' of the crusher-knife 40' runs straight through the grid-forming insert part 37', as shown in the drawing.

A grid 37a' formed by mutually crossing rods 37b' and 37c' is shown in the insert part 37'. With the grid 37a', one aims to catch macroorganisms upstream of the main component 29.

The rods can, in practice, extend further in the axial direction of the pipe piece 32' than in its radial direction, so that the grid 37' in addition can partially form knife-shaped rods and partially can form guiding bodies for the flow of liquid towards the rotating crusher-knife 40' arranged downstream. It is consequently possible to form an effective combination of a stationary and a rotary crusher device in a narrow area of the internal passage of the pipe piece 32'.

With the help of the rotary crusher-knife 40', one can provide an advantageous rotation of the flow of liquid from the additional component 29' to the main component 29 in the treatment installation according to the invention.

By arranging the crusher-forming component 29' upstream immediately in front of the main component 29, it is possible to carry out an effective subsequent treatment of all kinds of organisms in the flow of liquid via an alternating current field in the main component 29, i.e. including live organisms which may exist in divided up or crushed macroorganisms.

Tests have shown that the alternating current fields are more effective for microorganisms than for relatively large macroorganisms. A crushing or grinding of macroorganisms before the treatment with alternating current can consequently lead to increased effect by destroying remaining live organisms in the remains after the crushed or ground macroorganisms. The combination of components 29 and 29' can ensure that the ground remains of the macroorganisms can also be destroyed instantaneously in the main component 29 with an effect corresponding to that ensured for the microorganisms.

Alternatively, a pair of additional components 29', 29' in succession in the flow path through the treatment installation 26 can be used. The two sets of components 29', 29' can be formed with a mutually different, practical shape, for example, with different details, i.e. details of the crusher-knives and details of the grids and with different effects in the main component 29, respectively.

In addition, a second additional component, which can be connected to the main component 31' at its downstream end, can be used. This additional component can be equipped with an insert part approximately corresponding to the grid-forming insert part 37' as shown in FIG. 11. The grid-forming and crusher-forming insert part can alternatively be replaced by a filter or by a sequence of several filters or similar equipment to collect the remains of the destroyed organisms from the treatment in the main component 29.

To provide the longest possible length of movement for the flow of water through the treatment component, special rotation-promoting vanes or similar guiding arrangements can be built as an additional provision inside the case 48 or upstream, immediately in front of, or downstream, immediately behind, the respective alternating current field in the passage 49 in the case 48. By rotational movement, one can thereby ensure the flow of water a longer residence time inside the alternating current fields in the passage 49 of the case 48 and thereby a longer treatment time in the treatment component 29.

General Description of Testing Equipment.

Figure 12:
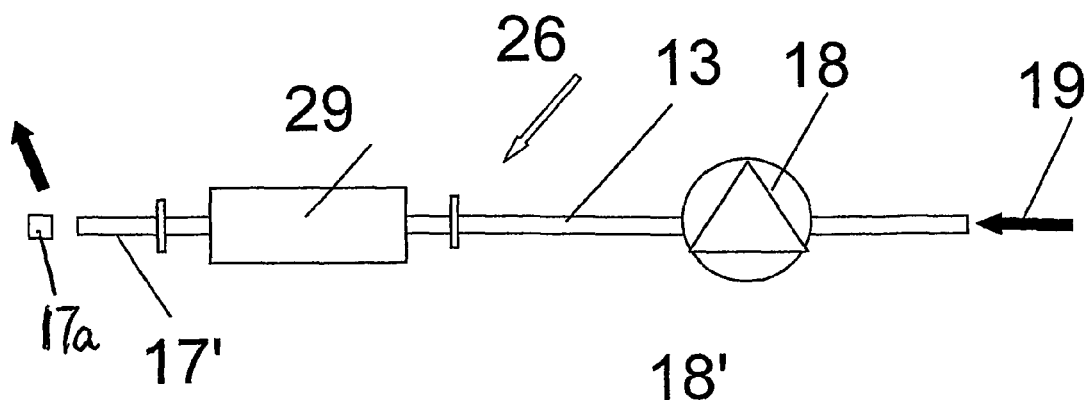
FIG. 12 shows schematically a first simple treatment installation which was used in connection with testing of water samples with the use of a pump and with treatment with the help of three-phase alternating current.
Figure 13:
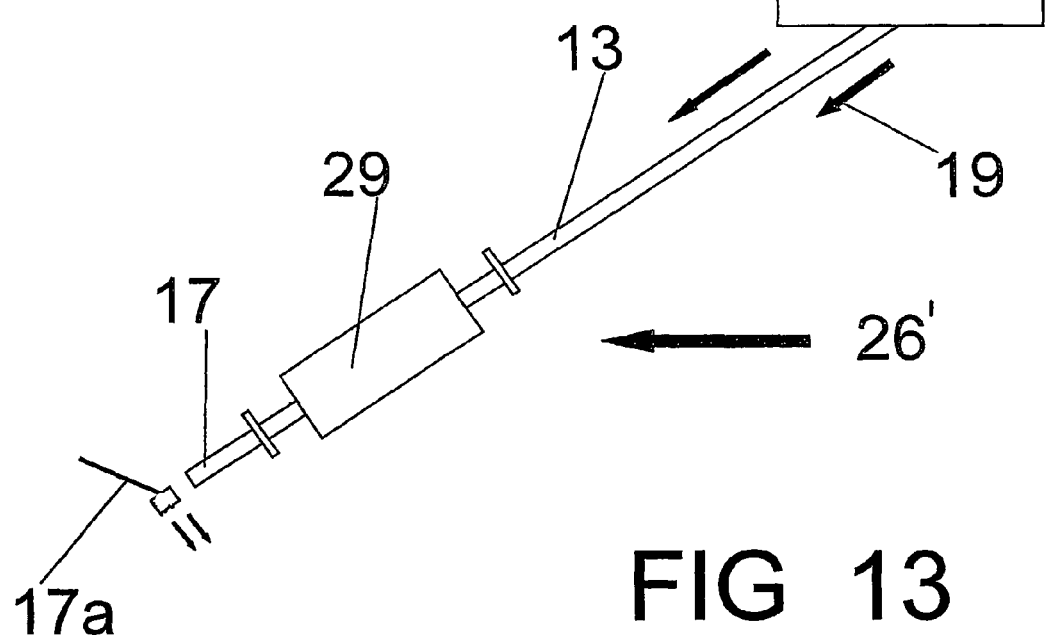
FIG. 13 shows schematically another simple treatment installation where the pump pressure is replaced by pipe pressure provided by water pressure in the water supply line and where the treatment is performed with the help of one-phase alternating current.

Reference is made to the drawings FIGS. 12 and 13, which show two simple treatment installations according to the invention.

The drawings show a treatment installation 26, 26' according to the invention, shown in two different embodiments, based on two different principles.

A mobile, easily replaceable treatment component 29 is used in both cases, corresponding to that shown in FIG. 5, with an extension in the axial direction of about 50 cm. Each of the components according to FIGS. 12 and 13 comprises a simple cylindrical piece of pipe with through-going passage corresponding to that shown in FIG. 9.

The electric conductor in a first embodiment example as shown in FIG. 12, is placed in a shape of a triangular corresponding to that shown in FIG. 10. In this example, the electric conductors are intended for transfer of three-phase alternating current to a flow of liquid through the installation. A pump 18 is shown corresponding to that shown in FIG. 1 at the upstream end of the pipeline 13, as liquid is sucked into the pump 18 from a liquid reservoir which is shown by the arrow 19 and discharged at the downstream end of the installation, as shown by 17.

The electric conductors in a second embodiment example, as shown in FIG. 13, are placed diametrically across from each other, as shown in FIG. 9a, for transfer of a one-phase alternating current to the flow of liquid through the associated piece of pipe.

Instead of the pump 18, as shown in FIG. 12, a liquid container 18', which is placed at the upstream end of the pipeline 13 as shown by the arrow 19, is used, as the liquid pressure provided by the shown inclined pipeline 13 and by the content of the liquid container 18' give the flow of water in the pipeline 13 a forced flow movement through the component 29.

At the downstream end of the pipeline, as shown at the outlet 17, a removable stopper 17a for initial closure of the downstream end of the pipeline 13 is shown.

In the first embodiment example, as shown in FIG. 12, a continuous flow of liquid is supplied in a forced movement through the treatment installation 26, provided by the pump 18 with inlet line connected to a water source, where the liquid in the embodiment example shown comprises seawater (salt water).

In the second embodiment example, as shown in FIG. 13, a liquid is supplied in portions to the liquid container 18'. After the outlet 17 is initially closed by means of the mentioned stopper 17a, the total pipeline 13 is filled with the liquid that is to be treated and the treatment starts at the same time as the stopper 17a opens the outlet 17. The treatment in the component 29 takes place by refilling of liquid from the liquid container 18', so that over a given time period, a forced flow of water through the passage in the treatment component 29 can be established.

Surprisingly, it has been found in performed tests with the treatment installation according to FIGS. 12 and 13, that one-phase, three-phase and zero-point alternating current mainly give corresponding results and that the different voltages that have been experimented in the tests do not give significant various results for the liquid treatment according to the invention. This indicates that it is possible to use various current voltages according to need at the individual location of use.

On the other hand, it has been found that the amperage gives various results and that, for example, an amperage of 13-16 Amp (Ampere) leads to a relatively poor result, while an amperage of 2540 Amp and higher leads to surprisingly good result, with apparently complete destruction of all live organisms in the liquid that is treated.

The pump 18 that was used in the first embodiment example which was shown in FIG. 12 and that is specially adapted for use in an installation for treatment of ballast water, had a capacity of 90 liters per second, i.e. 324 tonnes per hour. It is practically possible, with one and the same pump, to have a capacity that is three times as large, i.e. 270 liters per second, i.e. 1000 tonnes per hour. In the treatment installation 26, a single 5 inch (about 12.5 cm) supply line 13 was used to shift 324 tonnes per hour, while the treatment installation 26 could have been fitted with a pipe bundle (as shown in FIG. 5) comprising three 5 inch pipe branches, to shift three times as much water, i.e. about 1000 tonnes per hour.

Tests Performed at Treatment of Liquid with Alternating Current Field According to the Invention.

Test were performed at treatment of different kinds of liquids during application of the method according to the invention during application of installations and components according to the invention, as shown in the drawings FIGS. 12 and 13. The tests in the experiments described are performed with the use of standard power supply from the public utility network. In particular, in the two different examples, three-phase and one-phase alternating current, respectively, are used, with a voltage of 220 V (volt) at 50 Hz (Hertz).

Experiments performed in internal passages in a piece of pipe with internal diameter of 18 inches gave poor results, while passages in a pipe bundle with several pieces of pipe which each had an internal diameter of about 5-6 inches (12-16 cm) gave very satisfactory results.

One of the conclusions is that when liquid is to be treated in such large amounts a relatively large internal pipe diameter is required, i.e. with an internal diameter above 5-6 inches, instead of using a single passage with a large cross section area a pipe bundle with two or more pieces of pipe with their own passage running in parallel ought to be used, as shown in FIGS. 5-7.

Three different tests have been performed, namely:
1) Testing of ballast water, i.e. seawater,
2) testing of polluted fresh water, i.e. river water from a city environment, and
3) testing of sewage water, i.e. river water with direct entry of sewage.

The tests are performed according to two different principles, i.e. with and without use of pump, respectively. According to a first principle, which concerns test 1, reference is made to FIG. 12. According to a second principle, which concerns tests 2 and 3, reference is made to FIG. 13.

1) Testing of Seawater.

The testing was based on liquid samples that were collected in packaging in the form of 260 ml bacteria bottles and which were collected from a flow of liquid in a test installation as shown in FIG. 12.

Sample 1: Untreated water (with a bacteria content shown prior to the treatment according to the invention)
Sample 2: Test no. 1
Sample 3: Test no. 2
Sample 4: Test no. 3
Sample 5: Test no. 4

| Applied amperage (A-amp): | | 13A | 25A | 35A | 45A |
|---|---|---|---|---|---|
| Applied method: | 1 | 2 | 3 | 4 | 5 |
| Vibrio bacteria (TCBS) per litre | 74,000 | 70 | 0 | 0 | 0 |

The samples used in the tests 1-5 were especially based on control of the content of Vibrio bacteria, as this type of bacteria has been found to be especially difficult to destroy with other known destruction technologies. One concluded that by destroying Vibrio bacteria, one would also, in all probability, destroy other types of bacteria.

The tests 2-5 show, compared to test 1 that forms the starting point for the tests 2-5, that the content of Vibrio bacteria was reduced with a positive result with the use of an amperage of 13 Amp according to test 2, while the bacteria content with the use of other amperages of 25, 35 and 45 Amp, respectively, was reduced surprisingly greatly to a remarkably favourable result. All of the tests 3, 4 and 5, showed by analysis of the content of the experimental bottles, a result where apparently all the Vibrio bacteria were instantaneously destroyed. Other remaining live organisms could not be observed in the test samples either.

2) Testing of Uncleaned River Water.

The testing was based on samples of liquid which were collected in packaging in the form of 260 ml bacteria bottles and which were collected from a flow of liquid in an installation according to the invention.

Sample 1: Untreated water (with a content of bacteria shown prior to the treatment according to the invention).
Sample 2: Test no. 1

| Applied voltage: | 13 Amp | |
|---|---|---|
| Applied method: | 1 | 2 |
| Bacterial number/ml 36° C./44 h ISO 6222/mod | 520 | 62 |
| Coliform bacteria per 100 ml NS 4788 | ≧1000 | 6 |
| Thermo tolerant *coli* per 100 ml NS 4792 | 32 | 0 |

The testing shows that the content of coliform bacteria and thermo tolerant colibacteria were reduced with a surprisingly positive result with the use of an amperage of 13 A. In other words, one achieved a substantial reduction of the content of bacteria with the use of a relatively moderate amperage.

3) Testing of Sewage Water.

The testing was based on liquid samples which were collected in a packaging in the form of 260 ml bacteria bottles and which were collected from a flow of liquid in an installation according to the invention. The treatment installation depicted in FIG. 13 was used.

Sample 1: Untreated sewage water (with a content of bacteria shown prior to the treatment according to the invention).
Sample 2: Test no. 1.
Sample 3: Test no. 2.

| Applied voltage | | 13 Amp | 15 Amp |
|---|---|---|---|
| Applied method: | 1 | 2 | 3 |
| Thermo tolerant colibacteria Per 100 ml NS 4792 | 780,000 | ≧50,000 | ≧50,000 |

The tests showed that the content of thermo tolerant coliobacteria was reduced with a positive, yet not completely satisfactory result, with the use of a moderate amperage of 13 Amp and 15 Amp, respectively. Of a content of 780,000 thermo tolerant colibacteria in the liquid sample, apparently more than 730,000 thermo tolerant colibacteria were destroyed, but the results show that there was still a content of less than 50,000 thermo tolerant colibacteria after the treatment according to test 3. This gives in total a favourable cleaning effect of the sewage water. With an amperage difference of 2 Amp in the test methods 2 and 3, it was not possible to determine any essential difference in the result. It was found that increasing the amperage from 13 to 15 Amp did not have any significant effect on the result.

However, tests on practical samples have shown in a surprising way that one achieves considerably improved results with use of approximately twice as high amperage, for example, 25, 35 and 45 Amp, respectively. By application of all the three last mentioned amperages, one achieved an apparent 100% destruction of the bacteria, i.e. the same result was achieved with all three amperages of 25-45 Amp. The conclusion must be that the amperage used is very decisive and that the effect must be more secure the higher the amperage one uses. Another conclusion is that it was achieved a very favourable result with a rather moderate electricity consumption of 25 Amp, i.e. with rather low operating costs, for the smallest of the three amperage examples 25 Amp, 35 Amp and 45 Amp.

The consumption of electricity in treatment of microorganisms in water was at the same level as when one should treat water containing macroorganisms. This implies that both macroorganisms and microorganisms can be treated in one and the same operation and with a satisfactory result for both types of organisms in one and the same operation.

Experiments have been performed with pipes of different internal cross sectional diameter from 2 inches (about 5 cm) to 18 inches (about 46 cm). The best results were achieved with pipes with an internal cross sectional diameter of about 5 inches (about 12.5 cm) and pipes with even smaller cross sectional diameter, respectively.

Instead of a single piece of pipe with large diameter, a pipe bundle with several pipe branch running in parallel in a joined unit is preferred. Together, the pipe branches have approximately a cross sectional area that corresponds to the main pipe. The use of pipe branches with reduced cross sectional area instead of a single main pipe with a large cross sectional area offers a more favourable solution altogether. The distribution of the water flow in several pipe branches gives a more effective alternating current field in each pipe branch, i.e. in the whole of the cross sectional area of the pipe branch. Together, the pipe branches can give sufficient collected capacity corresponding to the capacity of the main pipe, without thereby substantially increasing the external dimensions of the pipe bundle. A special advantage is that with such a group of pipe branches instead of one single pipe, one can achieve a combined smaller electricity consumption and at the same time a better effect of the alternating current fields.

By using a number of pipe branches that gives an overcapacity in relation to the main pipe, one can, in addition, ensure a lower through-flow velocity and thereby a longer residence time in the treatment component. This ensures that the effect of the alternating current field will be better utilised over time, as the flow of water in such cases will be kept in motion over a longer period of time within the treatment component.

It is not required that the amount of water must pass the branch pipes with relatively large diameter or that the amount of water must be relatively large or must flow in a strong water stream, i.e. with a large pressure or with a high flow velocity. On the contrary, in certain cases it is an advantage to use low flow cross section, low flow velocity and low liquid pressure, as the operating costs are then considerably lower at the same time as the system is simpler to handle both in regard to operating safety, safety for the surroundings and the equipment itself as a consequence of the use of lower amounts of flow.

An essential concept, according to the invention, is that it is possible to treat even large amounts of water with a relatively large water pressure and with high flow velocity in an effective way.

According to the invention, even if there is a general need for watertight pipe connections in the installation, there are still possibilities for local drainage from the pipe connections via limited drain openings, even from the treatment component of the installation, for example, for intermittent taking of liquid samples from the treatment installation itself.

The invention claimed is:

1. An installation for the treatment of ballast water, said installation comprising
   a treatment component having an internal passage through which ballast water may flow and electrodes connected to an electric current source, characterised in that said treatment component comprises a bundle of pipes of electrically insulating material allowing for ballast water flow therethrough in parallel, and in that each said pipe is provided with said electrodes whereby ballast water flowing therethrough may be subjected to an electric current thereby to destroy live organisms therein; and
   a coat disposed about and encasing said bundle of pipes, said coat comprising coat parts movable about a hinge between open and closed positions.

2. An installation as claimed in claim 1 further comprising an electrical plug and socket mounted on said coat part and said bundle of pipes and wherein movement of a said coat part to an open position causes the electrical connection between said plug and socket to be broken.

3. An installation as claimed in claim 1 wherein said source is an alternating current source.

4. An installation as claimed in claim 3 wherein said source is a one-phase, three-phase or zero point alternating current source.

5. An installation as claimed in claim 4 wherein said source is a three-phase alternating current source.

6. An installation as claimed in claim 1 wherein in each pipe of said bundle of pipes the said electrodes are arranged in a triangular pattern in a plane crossing the ballast water flow direction.

7. An installation as claimed in claim 1 further comprising a pump for pumping ballast water through said component.

8. An installation as claimed in claim 1 wherein said source and electrodes are arranged to supply current to ballast water flowing through said bundle of pipes at a level of (25 to 40)/90 Amps per liter flowing through said component per second.

9. An installation as claimed in claim 1 wherein said component further comprises inlet and outlet pipes and wherein ballast water may flow sequentially through said inlet pipe, said bundle of pipes, and said outlet pipe.

10. An installation as claimed in claim 9 wherein the internal cross-sectional area of said inlet pipe is about the same as the combined internal cross-sectional areas of said pipes in said bundle.

11. An installation as claimed in claim 9 wherein the internal cross-sectional area of said inlet pipe is less than the combined internal cross-sectional areas of said pipes in said bundle.

12. A ballast water treatment unit for a ballast water treatment installation, said unit comprising an internal passage through which ballast water may flow and electrodes, characterised in that said unit is mountable in and dismountable from said installation, in that said unit comprises a bundle of pipes of electrically insulating material allowing for ballast water flow therethrough in parallel, and in that each said pipe is provided with said electrodes whereby ballast water flowing therethrough may be subjected to an electric current thereby to destroy live organisms therein and further comprising a coat disposed about and encasing said bundle of pipes said coat comprising coat parts movable about a hinge between open and closed positions.

13. A unit as claimed in claim 12 further comprising ballast water inlet and outlet pipes, wherein the internal cross-sectional area of said inlet pipe is about the same as the combined internal cross-sectional areas of the pipes of said bundle of pipes.

14. A unit as claimed in claim 12 further comprising ballast water inlet and outlet pipes, wherein the internal cross-sectional area of said inlet pipe is less than the combined internal cross-sectional areas of the pipes of said bundle of pipes.

15. A unit as claimed in claim 12 further comprising an electrical plug and socket mounted on said coat part and said bundle of pipes whereby movement of a said coat part to an open position causes the electrical connection between said plug and socket to be broken.

16. A unit as claimed in claim 12 wherein in each pipe of said bundle of pipes the said electrodes are arranged in a triangular pattern in a plane crossing the ballast water flow direction.

* * * * *